United States Patent [19]

Ferro et al.

[11] Patent Number: 5,416,250
[45] Date of Patent: May 16, 1995

[54] GENETIC CONTROL OF ETHYLENE BIOSYNTHESIS IN PLANTS USING S-ADENOSYLMETHIONINE HYDROLASE

[75] Inventors: Adolph J. Ferro, Lake Oswego; Richard K. Bestwick, Portland; Lyle R. Brown, Corvallis, all of Oreg.

[73] Assignee: Agritope, Inc., Beaverton, Oreg.

[21] Appl. No.: 255,833

[22] Filed: Jun. 8, 1994

Related U.S. Application Data

[63] Continuation of Ser. No. 613,858, Dec. 12, 1990, abandoned, which is a continuation-in-part of Ser. No. 448,095, Dec. 12, 1989, abandoned.

[51] Int. Cl.$^6$ .................. A01H 4/00; C12N 15/82
[52] U.S. Cl. .................. 800/205; 435/172.3; 435/320.1; 435/240.4
[58] Field of Search .............. 536/23.2, 23.7; 435/172.3, 252.3, 290.4, 320.1; 800/205, DIG. 43

[56] References Cited

U.S. PATENT DOCUMENTS 4,769,061  9/1988  Comai ............... 435/172.3

OTHER PUBLICATIONS

Hughes et al. (Aug. 1987) Journal of Bacteriology 169(8): 3625–3632.
Kushad et al (1983) Plant Physiology 73: 257–261.
Kozak (Jan. 31, 1986) Cell 44: 283–292.
Potrykus (Jun. 1990) Bio/Technology 8: 535–542.
Gelvin (1987) Plant Molecular Biology 8: 355–359.
Vaeck et al. (Jul. 1987) Nature 328: 33–37.
Fischhoff et al. (1987) Bio/Technology 5: 807–813.
Spoerel, et al., Colivirus-T3-Coded S-Adenosylmethionine Hydrolase, Eur. J. Biochem. 95, pp. 227–233, 1979.
Hughes, et al., Expression of the Cloned Coliphage T3 S-Adenosylmethionine Hydrolase Gene Inhibits DNA Methylation and Polyamine Biosynthesis in *Excherichia coli*, Journal of Bacteriology, pp. 3625–3632, 1987.
Hooykaas, Transformation of Plant Cells via Agrobacterium, Plant Molecular Biology 13, pp. 327–336, 1989.
Kozak, Point Mutations Define a Sequence Flanking the AUG Initiator Codon that Modulates Translation by Eukaryotic Ribosomes, Cell. vol. 44, pp. 283–292, 1986.
Melchers, et al., Nuclotide Sequence of the Virulence gene virG of the Agrobacterium tumefaciens Octopine Ti plasmid: Significant homology between virG and the Regulatory genes ompR, phoB and dye of *E. Coli*, Nucleic Acid Research, vol. 14, No. 24 pp. 9933–9942, 1986.

(List continued on next page.)

Primary Examiner—Che S. Chereskin
Attorney, Agent, or Firm—Gary R. Fabian

[57] ABSTRACT

A method for control of ethylene biosynthesis in plants comprising a vector containing a selective gene under plant promoter control, and a DNA insert comprising codons for a functional heterologous polypeptide having AdoMetase activity and flanked by a plant promoter on one side and a polyA signal sequence on the other side; and, transforming a plant host with said vector wherein the plant host transformed thereby is capable of expressing the heterologous polypeptide having AdoMetase activity under the control of said control region. The presence of the AdoMetase gene and the expression of AdoMetase in transgenic plants lowers AdoMet levels and generates an inhibitor of ACC synthase causing a corresponding decrease in ethylene biosynthesis and precursor availability. The current construction of transgenic plants containing a copy(s) of the T3 AdoMetase gene allow for construction of plants that will control ethylene biosynthesis under restricted conditions resulting in fruits, vegetables, and flowers which have been modified internally to improve shelf life and preservation qualities.

10 Claims, 8 Drawing Sheets

OTHER PUBLICATIONS

Kushad, et al., 5-Methylthioribose Kinas Activity in Plants, Biochemical and Biophysical Research Comm., vol. 108, No. 1, pp. 167–173, 1982.

Winans, et al., A gene essential for Agrobacterium virulence is homologous to a family of positive regulatory loci, Proc. Natl. Acad. Sci., USA, vol. 83, pp. 8278–8282, 1986.

Bevan, Binary Agrobacterium vectors for Plant Transofmration, Nucleic Acids Research, vol. 12, No. 22, pp. 8711–8721, 1984.

Zambryski, et al., Transfer and Function of T-DNA genes from Agrobacterium Ti and Ri plasmids in Plants, Cell, vol. 56, pp. 193–201, 1989.

Kushad, et al., Role of the 5' methylthioadenosine to S-adenosylmethionine salvage pathway in wound ethylene formation, Plant Physiology, vol. 89, p. 113, Abstract 671, 1989.

Kushad, et al., 5'-methylthioadenosine Nucleosidase and 5-Methylthioribose Kinase Activities and Ethylene Production During Tomato Fruit Development and Ripening, Plant Physiol., vol. 79, pp. 525–529, 1985.

Kushad, et al., Intermediates in the Recycling of 5-Methylthioribose to Methionine in Fruits, Plant Physiol., vol. 73, pp. 257–261, 1983.

Hughes, et al., Nucleotide sequence and analysis of the coli phage T3 S-adenosylmethionine hydrolase gene and its surrounding ribonuclease III processing sites, Nucleic Acids Research, vol. 15, pp. 717–729, 1987.

```
                                                                    XhoII
                                                                    Sau3AI
                                                    TaqI            | NlaIV
                                                    SalI   XbaI     NdeII
                                                    | MnlI|         MboI
                                                    PstI|HinfI      CpfI
                    HindIII                         |   HincII      BstI
                    EcoVIII    SphI                 |   |           BamHI
        AluI        | AluI     NlaIII               AccI| MaeI      | |
        |    NlaIII | |        |                    |||  ||         | |
      1 ACAGCTATGACCATGATTACGCCAAGCTTGCATGCCTGCAGGTCGACTCTAGAGGAT      57

XmnI
            NcoI              MboII         Asp700       RsaI
            |                 |             |            |
     58 CCGCCACCATGGTTTTCACTAAAGAGCCTGCGAACGTCTTCTATGTACTGGTTTCCG       114
          METValPheThrLysGluProAlaAsnValPheTyrValLeuValSerA

MnlI    MnlI           HphI              NlaIII
                    |       |              |                 |
    115 CTTTCCGTTCTAACCTCTGCGATGAGGTGAATATGAGCAGACACCGCCACATGGTAAGCA   174
         laPheArgSerAsnLeuCysAspGluValAsnMETSerArgHisArgHisMETValSerT

ScrFI
                NciI                                    ScrFI
            MspI                                        NciI
            HpaII            HinfI                      MspI
        Fnu4HI|              |      NlaIV   HincII      HpaII  MnlI
        |    ||              |      |       |           ||      |
    175 CTTTACGTGCCGCACCGGGTCTTTATGGCTCCGTTGAGTCAACCGATTTGACCGGGTGCT   234
         hrLeuArgAlaAlaProGlyLeuTyrGlySerValGluSerThrAspLeuThrGlyCysT MnlI
            HinPlI
            | HhaI
            | CfoI    DdeI                    RsaI
            | ||      |                       |
    235 ATCGTGAGGCAATCTCAAGCGCACCAACTGAGGAAAAAACTGTTCGTGTACGCTACAAGG   294
         yrArgGluAlaIleSerSerAlaProThrGluGluLysThrValArgValArgTyrLysA
```

*FIG. 6*

```
                HinPlI
                  HhaI
                   Fnu4HI                  MaeI
                    CfoI      BbvI           |  AluI
                     |         |             |   |
    295 ACAAAGCGCAGGCACTCAATGTTGCACGCCTAGCTTGTAATGAGTGGGAGCAAGATTGCG 354
        spLysAlaGlnAlaLeuAsnValAlaArgLeuAlaCysAsnGluTrpGluGlnAspCysV
```

```
        RsaI  AccI        HinfI                 RsaI            TaqI
         |     |            |                    |               |
    355 TACTGGTATACAAATCACAGACTCACACGGCTGGTCTGGTGTACGCTAAAGGTATCGACG 414
        alLeuValTyrLysSerGlnThrHisThrAlaGlyLeuValTyrAlaLysGlyIleAspG
```

```
                          ScrFI                        HinPlI
                          NciI                          HhaI
                          MspI              NlaIV       CfoI
                          HpaII    MnlI    | BbvI      | BbvI    Fnu4HI
                           ||       |      |  |        |  |       |
    415 GGTATAAGGCTGAACGTCTGCCGGGTAGTTTCCAAGAGGTTCCTAAAGGCGCACCGCTGC 474
        lyTyrLysAlaGluArgLeuProGlySerPheGlnGluValProLysGlyAlaProLeuG
```

```
             Fnu4HI                  Fnu4HI       RsaI
               |                       |            |
    475 AAGGCTGCTTCACTATTGATGAGTTCGGTCGCCGCTGGCAAGTACAATAAGTGTTA      531
        lnGlyCysPheThrIleAspGluPheGlyArgArgTrpGlnValGln***
```

```
                                                      TaqI
                                                      SstI
                                           RsaI       SacI
                                 Sau3AI   NlaIV       HgiAI
                                 NdeII   | KpnI       EcoRI
                                 MboI    | BanI|      BanII
            SfaNI  NlaIII        CpfI   Asp718  AluI|  |
              |     |             |      | | |   | | |
    532 AACTCAAGGTCATGCACGATGCGTGGCGGATCGGGTACCGAGCTCGAATTCACTGG     586
```

*FIG. 6 (cont.)*

GENETIC CONTROL OF ETHYLENE BIOSYNTHESIS IN PLANTS USING S-ADENOSYLMETHIONINE HYDROLASE

This application is a file-wrapper-continuation of U.S. patent application Ser. No. 07/613,858, filed 12 Dec. 1990, now abandoned, which is a continuation-in-part of U.S. patent application Ser. No. 448,095, filed 12 Dec. 1989, now abandoned.

BACKGROUND OF THE INVENTION

This invention relates to a method and means of genetic control of ethylene biosynthesis in plants.

Ethylene is a plant hormone influencing many aspects of plant growth and development. This simplest of all unsaturated carbon compounds is a powerful regulator of plant metabolism, acting, and interacting with other plant hormones in trace amounts.

Ethylene promotes senescence in plants, both in selected groups of cells and in whole organs such as fruits, leaves, or flowers. Senescence is the natural, genetically controlled degenerative process which usually leads to death in plants. Even at low concentrations (ethylene is a gas under physiological conditions), ethylene has profound hormonal effects on plants. The effects of ethylene, whether produced by the plant itself or applied exogenously, are numerous, dramatic, and of considerable commercial importance. Among the diverse physiological effects are:

a. Stimulation of ripening in fruits and vegetables
b. Leaf abscission
c. Fading in flowers
d. Flower wilting
e. Leaf yellowing
f. Leaf epinasty Normally, ethylene production from plant tissue is low. Large quantities of ethylene, however, are produced during ripening and senescence processes. A large amount of ethylene is also produced following trauma caused by chemicals, temperature extremes, water stress, ultraviolet light, insect damage, disease, or mechanical wounding. Ethylene produced by plants under such conditions is referred to as "wound ethylene" or "stress ethylene". In fruits and vegetables, the stimulation of ethylene production by cuts or bruises may be very large and bear considerably on storage effectiveness. Ethylene-induced leaf browning is a common basis for loss in many plants, including lettuce and tobacco. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

The mechanism by which ethylene exerts its effects has become apparent only in the last few years. As judged by numerous data, each of the responses to ethylene involves an ethylene receptor site—a metalloenzyme. The reaction of ethylene with its receptors triggers a cascade of physiological events. Marked increases in the amounts of RNA and protein occur in response to ethylene. The levels of several enzymes have also been shown to increase in response to ethylene, such as cellulase, α-amylase, and invertase.

Current technologies that specifically address postharvest storage life have been in existence for decades and are hampered by such problems as high cost, side effects, and an inability to completely shut off ethylene production. Included in this group are controlled atmosphere (CA) storage, chemical treatment, packaging, and irradiation.

CA facilities slow ethylene biosynthesis through: (1) low temperature, (2) reducing the oxygen level below 3%, and (3) elevating the carbon dioxide level in the storage area to the 3%–5% range. Expensive scrubbers are sometimes added which reduce ethylene already respired to the atmosphere. Drawbacks are that CA facilities are expensive to construct, have a high utility cost, and are unable to completely eliminate ethylene production and side effects. Also, CA storage techniques can only control external ethylene and not that which resides inside the plant tissue. CA storage can also lead to undesirable side effects. Injury can result from high $CO_2$ levels, low $O_2$ levels, or low temperature.

Another approach is to limit ethylene biosynthesis in the plant tissue through chemical treatment. Aminoethoxyvinylglycine (AVG), an analog of the antibiotic rhizobitoxine, is such an inhibitor. Use of the chemical in foods is impossible, however, due to its high toxicity. Silver thiosulfate (STS) is also effective in slowing fruit ripening and flower fading but is also toxic and cannot be used on foods. STS only works with certain flowers and often causes black spotting.

The amino acid methionine has been shown to be a precursor of ethylene in plant tissues. Methionine, however, is not the immediate precursor, but first must be converted to the sulfonium compound S-adenosylmethionine (AdoMet) and, subsequently to 1-aminocyclopropane-1 carboxylic acid (ACC) prior to conversion to ethylene. The following metabolic reactions (also see FIG. 1) are now accepted for the synthesis of ethylene from methionine under both normal and stress conditions:

Methionine→AdoMet→ACC→Ethylene

The system which converts ACC to ethylene appears to be constitutive in most plant tissues with the notable exception of some preclimacteric fruit tissue. ACC synthase catalyzes the degradation of AdoMet to ACC and 5'-methylthioadenosine (MTA). This enzymatic reaction seems to be the rate limiting step in ethylene formation. AdoMet is synthesized via a condensation reaction between methionine and Adenosinetriphosphate (ATP). Attempts at regulating the levels of AdoMet by controlling the rate of AdoMet synthesis have failed, mainly because there appear to be at least three different AdoMet synthesizing enzymes coded by three different genes. In addition, the known biochemical inhibitors of AdoMet synthesis are very toxic to mammalian cells. See S. F. Yang, et al., "Ethylene Biosynthesis and its Regulation in Higher Plants," *Ann. Rev. Plant Physiol,* 35:155–189, 1984; Veen, et al., *SciHortic,* 18:277–286; Sisler, et al, *Plant Physiol,* 63:114–120; and Wang, et al., *Plant Physiol,* 89:434–438.

Although plant tissues are known to maintain a substantial rate of ethylene production for extended periods, their methionine levels have been shown to be very low. To continue to produce ethylene, the sulfur contained in MTA must be recycled back into methionine so as to provide an adequate supply of methionine for continual ethylene production. This pathway has been recently shown to exist in plant tissue (see FIG. 1c). See also S. F. Yang, et al., "Ethylene Biosynthesis and its Regulation in Higher Plants," *Ann. Rev. Plant Physiol*, 35:155–189, 1984. The degradation of MTA has added significance in light of the finding that MTA is a potent inhibitor of ACC synthase. It should be noted that this pathway merely maintains a methionine supply for ethylene biosynthesis, but does not result in a net increase in methionine synthesis.

An enzyme encoded by the *E. Coli* bacteriophage T3 hydrolyzes S-adenosylmethionine (AdoMet) to homoserine and 5'-methylthioadenosine (MTA). This enzyme is known by either its recommended name, AdoMet hydrolase (AdoMetase), or by its other name, S-adenosylmethionine cleaving enzyme (SAMase). See Studier, et al., "SAMase Gene of Bacteriophage T3 is Responsible for Overcoming Host Restriction," *Journal of Virology*, 19:135–145, 1976. Both products of the reaction are recycled to methionine; MTA as previously shown (FIG. 1) and homoserine via a metabolism pathway known to exist in plant tissues. The AdoMetase gene has been identified, isolated, cloned, and sequenced. J. A. Hughes, et al., "Expression of the Cloned Coliphage T3 S-adenosylmethionine Gene Inhibits DNA Methylation and Poly Amine Biosynthesis in *Escherichia coli*", J. Bact., 169:3625–3632, 1987 and J. A. Hughes, et al., "Nucleotide Sequence and Analysis of the Coliphage T3 S-adenosylmethionine Hydrolase Gene and its Surrounding Ribonuclease III Processing Sites", *Nuc. Acids Res.*, 15:717–729, 1987. The gene contains two inframe reading sequences that specify polypeptides of 17105 and 13978 daltons. Both polypeptides terminate at the same ochre codon. This results in the 14 kd polypeptide being identical to 82% of the 17 kd polypeptide starting at the carboxyl end of the longer polypeptide. Both polypeptides are present in partially purified preparations of active AdoMetase from T3 bacteriophage infected cells and from *E. Coli* expressing the cloned gene. J. A. Hughes, et al., "Nucleotide Sequence and Analysis of the Coliphage T3 S-adenosylmethionine Hydrolase Gene and its Surrounding Ribonuclease III Processing Sites," *Nuc. Acids Res.*, 15:717–729, 1987 and F. W. Studier, et al., "SAMase Gene of Bacteriophage T3 is Responsible for Overcoming Host Restriction ," *J. Virol.*, 19:136–145, 1976.

Other bacteriophages that encode the AdoMetase or SAMase genes are coliphage BA14, Klebsiella phage K11, and Serratia phage IV. See H. Mertens, et al., "Coliphage BA14: a New Relative of Phage T7," *J. Gen. Virol.*, 62:331–341, 1982; R. Hausmann, *The Bacteriophages*, 1:279–283, 1988, R. Calender (ed.), Plenum Press, New York; and K. H. Korsten, et al., "The Strategy of Infection as a Criterion for Phylogenetic Relationships of Non-Coli Phages Morphologically Similar to Phage T7," *J. Gen. Virol.*, 43:57–73, 1979.

SUMMARY OF THE INVENTION

AdoMetase is normally not present in plant tissues. The AdoMetase gene codes for a protein having a very unusual enzymatic activity. Bacteriophage T3, Coliphage BA14, Kiebsiella phage K11, and Serratia phage IV are the only known sources of a gene encoding that activity. The presence of the AdoMetase gene and the expression of AdoMetase in transgenic plants lowers AdoMet levels. This effect is shown schematically in FIG. 1*b*. Since AdoMet is the sole precursor for ethylene biosynthesis, its reduced availability causes a corresponding decrease in ethylene biosynthesis. Furthermore, the hydrolysis of AdoMet by AdoMetase generates MTA which is an inhibitor of ACC synthase, a principle enzyme in the biosynthesis of ethylene by plants. The net effect is twofold, a reduction in precursor availability and a direct inhibition of ethylene biosynthesis. The current construction of transgenic plants containing at least one copy of the T3 AdoMetase gene by use of the Agrobacterium transfer systems allow for construction of plants that will control ethylene biosynthesis under restricted conditions. Thus, the present invention combines expertise from two very different fields of study, bacteriophage biochemistry, and plant biochemistry. This invention will result in fruits, vegetables, and flowers which have been modified internally to improve shelf life and preservation qualities.

The present invention relates to a vector useful for transformation of a plant host comprising a broad host-range plasmid containing a selective gene under plant promoter control. The vector also includes a DNA insert comprising codons for a functional heterologous polypeptide having AdoMetase activity, or a heterologous polypeptide having substantially the same biological activity as AdoMetase. The heterologous polypeptide is flanked by a plant promoter on one side and a PolyA signal sequence on the other side. The result is the transformed plant host is capable of expressing the heterologous polypeptide under the control of the control region. The DNA codons may be obtained from cDNA or genomic DNA, or may be prepared by DNA synthesis techniques.

The present invention further relates to a binary vector system useful for the transformation of a plant host comprising a "T-DNA less" Ti plasmid, and a broad host-range plasmid containing T-DNA borders, and a selective gene under plant promoter control. The vector also includes a DNA insert comprising codons for a functional heterologous polypeptide having AdoMetase activity, or a heterologous polypeptide having substantially the same biological activity as AdoMetase. The heterologous polypeptide is flanked by a plant promoter on one side and a polyA signal sequence on the other side. The result is the transformed plant host is capable of expressing the heterologous polypeptide under the control of the control region.

The present invention further relates to a tripartite vector system useful for transformation of a plant host comprising (a) a "T-DNA less" Ti plasmid, (b) a broad host-range P incompatibility group plasmid containing a cloned virG gene, and (c) a broad host-range plasmid containing T-DNA borders, and a selective gene under plant promoter control. The vector also includes a DNA insert comprising codons for a functional heterologous polypeptide having AdoMetase activity, or a heterologous polypeptide having substantially the same biological activity as AdoMetase activity, or functional derivatives thereof. The heterologous polypeptide is flanked by a plant promoter on one side and a polyA signal sequence on the other side. The result is the transformed plant host is capable of expressing the heterologous polypeptide under the control of said control region. See *Cell*, 56:193–201. Specifically, it has been constructed using a strain of Agrobacterium PC2760 containing a T-DNA-less derivative of pTiA6NC. To this transfer system has been added a plasmid pVK102 containing a plasmid pTiBo542 virG gene insert. This insert enhances the transfer of the DNA containing T-DNA borders that are contained on a third plasmid be it pGA 482-Sam-K or pBI 121-AdoMetase. In summary, the transfer system is provided by three plasmids all contained in the same bacterial strain. The first contains all of the genetic information needed to transfer genes to plants except it lacks the T-DNA borders. The second plasmid contains extra copies of one of the virulence genes which enhances the transfer process. The third plasmid contains the DNA to be delivered to the plants cells engineered between two T-DNA borders. This system differs from those published in that it uses three plasmids and a mixture of virulence gene products (ones from pTiA6NC and pTiBo542) to achieve efficient transfer to a broad variety of plants.

BRIEF DESCRIPTION OF THE DRAWINGS

The invention itself, as well as additional advantages and features thereof, will be more readily and comprehensively understood from the following detailed description of the preferred inventive embodiments, such description making reference to the appended sheets of drawings, wherein:

FIG. 6 indicates that part of the nucleotide sequence of pUC19SAM-K that encodes AdoMetase gene with the modified 5' end.

DESCRIPTION OF THE PREFERRED EMBODIMENT

Figure 2:
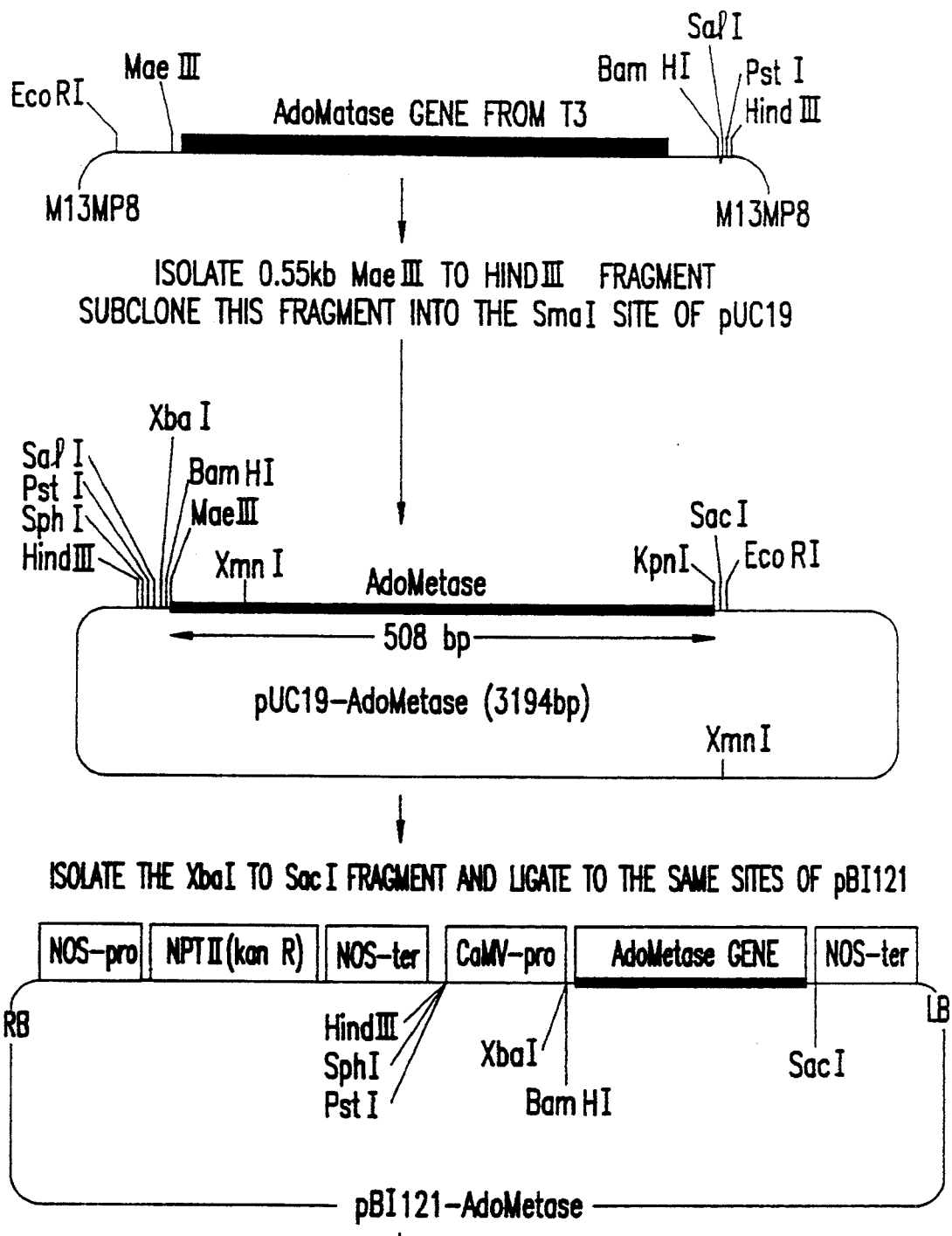
FIG. 2 schematically represents the construction of pBI121-AdoMetase.

The plant vector system consists of the following. To transfer the AdoMetase gene into plants, a binary *Agrobacterium tumefaciens* system is preferably used. The Agrobacterium strain PC2760 containing a "T-DNA less" Ti plasmid and a broad host-range plasmid containing T-DNA borders, a selective kanamycin gene under plant promoter control, and the AdoMetase gene flanked by a plant promoter on one side, and a polyA signal sequence on the other side is constructed as shown in FIG. 2 and described in the following examples.

It will be appreciated that the AdoMetase gene can be isolated from more than one bacteriophage. Different bacteriophages may be expected to contain AdoMetase genes with variations in their DNA sequences. Furthermore, the amino acid sequence of AdoMetase may be modified by genetic techniques to produce enzymes with altered biological activities. An increase in the biological activity could permit the use of lower amounts of the enzyme to control ethylene biosynthesis in plants. Modifications of the sequence of the AdoMetase gene are within the scope of the present invention.

EXAMPLE 1

The source of the AdoMetase gene is obtained and manipulated as follows. The AdoMetase gene has been identified on an AluI-HaeIII restriction fragment from purified T3 DNA (J. A. Hughes, et al., "Expression of the Cloned Coliphage T3 S-adenosylmethionine Gene Inhibits DNA Methylation and Poly Amine Biosynthesis in *Escherichia Coil*," J. Bact., 169:3625–3632, 1987). Bacteriophage T3 is available under ATCC No. 11303-B3. This DNA fragment was first cloned into the bacteriophage M13 MP8 vector (Pharmacia LKB Biotechnology, Inc.). A Mae 111 to Bam fragment is then subcloned into the pUC19 plasmid vector (Pharmacia) to produce pUC19-AdoMetase (pUC19-SAMase), transformed into *E. Coli* and used as a source of DNA for further construction experiments and for DNA sequence determination. The Mae 111 site is used as the 5' terminus of the AdoMetase gene fragment since it is only 10 base pairs upstream from the initiation codon for the gene. As shown in FIG. 2, pUC19-AdoMetase is used as the source of the AdoMetase gene for insertion into an *Agrobacterium tumefaciens* vector as described below.

The parent vector, pBI121, is obtained commercially from Clontech Laboratories, Inc. The plant promoter upstream of the AdoMetase gene sequence can be varied to obtain tissue specific expression, temperature dependent expression, low or high level constitutive expression, hormone-induced expression, or light dependent expression in the transgenic plants. In the following example, the promoter is the constitutive Cauliflower Mosaic Virus (CaMV) promoter (Pharmacia).

EXAMPLE 2

The following is an example of the construction and transformation with PC2760/pBI121-AdoMetase. The pUC19-AdoMetase plasmid is digested with Xba I and Sac I to produce a 520 bp fragment encoding the entire AdoMetase gene. The DNA fragment is purified by agarose gel electrophoresis followed by electrolution. The vector, pBI121, is also digested with Xba I and Sac I and purified by the same method as described above. The two fragments are ligated together and the resultant plasmid named pBI121-AdoMetase. PBI121-AdoMetase is introduced into Agrobacterium using a direct transformation method. *Agrobacterium tumefaciens* PC2760 is deposited with the American Type Culture Collection, Rockville, Md., under accession number ATCC 68111. *Agrobacterium tumefaciens* strain PC2760 is grown to mid log phase (OD 600 0.5 to 1.0) in YEP media (10 g yeast extract, 10 g peptone, and 5 g NaCl per liter). After chilling on ice, 50 mls of these cells are pelleted, resuspended in 1 ml of ice cold 20 mM $CaCl_2$ and split into 1 ml aliquots. One µg of pBI121-AdoMetase is added to one of the aliquots and incubated on ice for 30 minutes, frozen in liquid nitrogen and thawed at 37° C. for 5 minutes. One ml of YEP media is added and incubated at 28° C. for 2 hours. The cells are pelleted and resuspended in 50 µl of YEP, then plated on YEP agar plates containing 20 µg/ml kanamycin. Kanamycin-resistant transformed colonies appear within 2 days.

Figure 5:
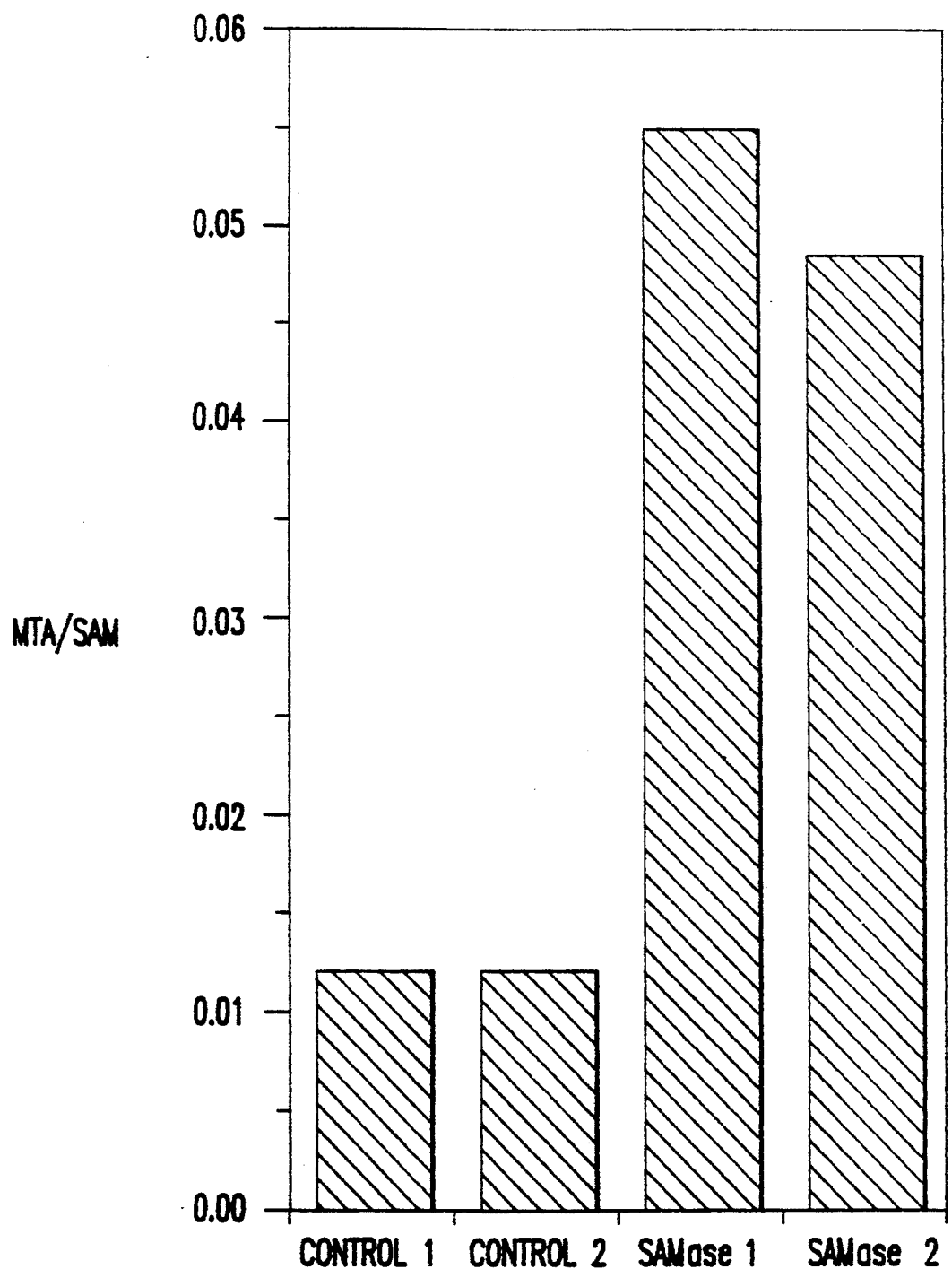
FIG. 5 indicates SAMase activity in transgenic plants.

A PC2760 clone containing these plasmids is named PC2760/pBI121-AdoMetase and was used to transform leaf discs obtained from Nicotiana tabacum L. cv. Wisconsin by the following direct method. A tobacco leaf is washed once in 95% ethanol for 10 seconds, once in 10% bleach, 0.1% Tween-20 for 20 minutes, four times in water, cut into 5 mm discs, and finally placed in a 10 ml overnight culture of PC2760/pBI121 for 30 minutes. The leaf discs are then placed on Murishegee and Sckoog callus forming medium for 1 day. The discs are then soaked in 500 µg/ml cefatoxamine for 1 hour and placed on Tobacco callus-forming media containing 200 µg/ml carbenicillin for 3 days. The discs are then transferred to the same medium containing an additional 100 μg/ml kanamycin. Kanamycin-resistant tobacco callus is selected using standard techniques. The regeneration of plants from calli is a known art. Protocols vary with each plant species and specific parameters can be easily determined by one skilled in the art. Plant tissues derived from this callus are shown to contain the AdoMetase gene using DNA-dot blots and Southern blots. Transcription of this gene is demonstrated by extracting RNA from lead tissue and performing Northern blots. Both Southern and Northern blots are probed with a radioactively-labeled AdoMetase gene fragment from pUC19-AdoMetase. The presence of AdoMetase enzyme is confirmed by making crude extracts from leaf tissue and performing AdoMetase assays as previously described and as demonstrated in FIG. 5 where extracts of transgenic plants were analyzed for enzymatic activity based on the ratio of 5'-methylthioadenosine to S-adenosylmethionine. Also demonstrated is the effect of Naphthaleneacetic acid (NAA), a plant hormone which stimulates ethylene production, on control tissues versus transgenic plant tissue in terms of ethylene evolution in tobacco leaf discs after 40 hours of culture. The transgenic tissue is designated Nt-BOB. The transgenic plant shows a marked decrease in ethylene evolution as shown in TABLE 1.

TABLE 1

The Effect of NAA on Ethylene Evolution of AdoMetase Transformed Tobacco Leaf Discs After 40 Hours of Culture

| Tissue | NAA (mM) | Ethylene (nmol/g/40 h) |
|---|---|---|
| Nt-control | 0.00 | 1.90 |
|  | 0.01 | 10.01 |
|  | 1.00 | 75.47 |
| Nt-BOB | 0.00 | 0.61 |
|  | 0.01 | 5.17 |
|  | 1.00 | 13.01 |

Figure 1A:
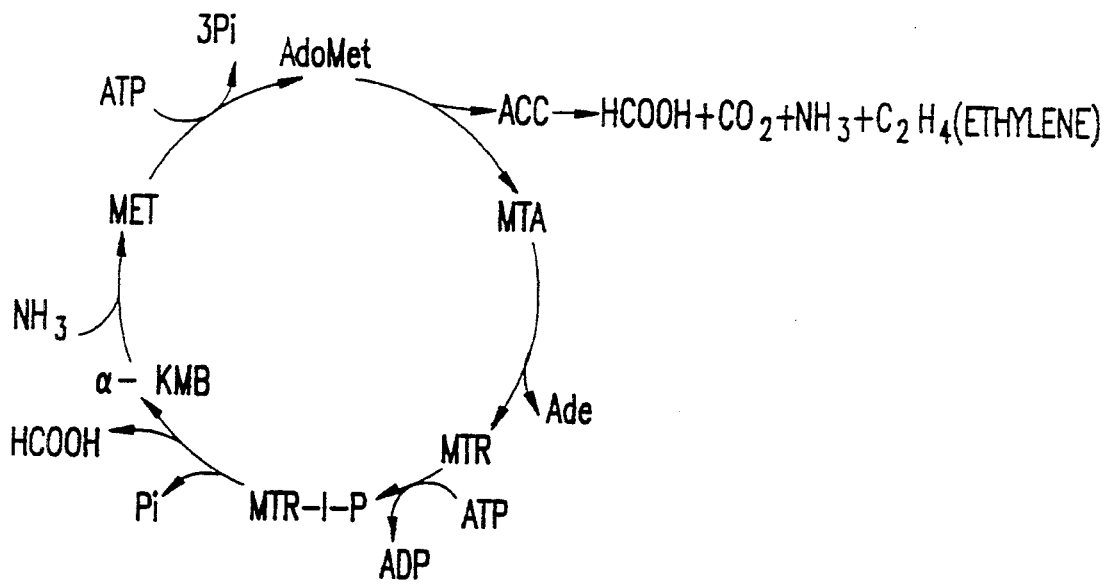
FIG. 1a schematically represents the ethylene biosynthetic pathway in plant tissue.
Figure 1B:
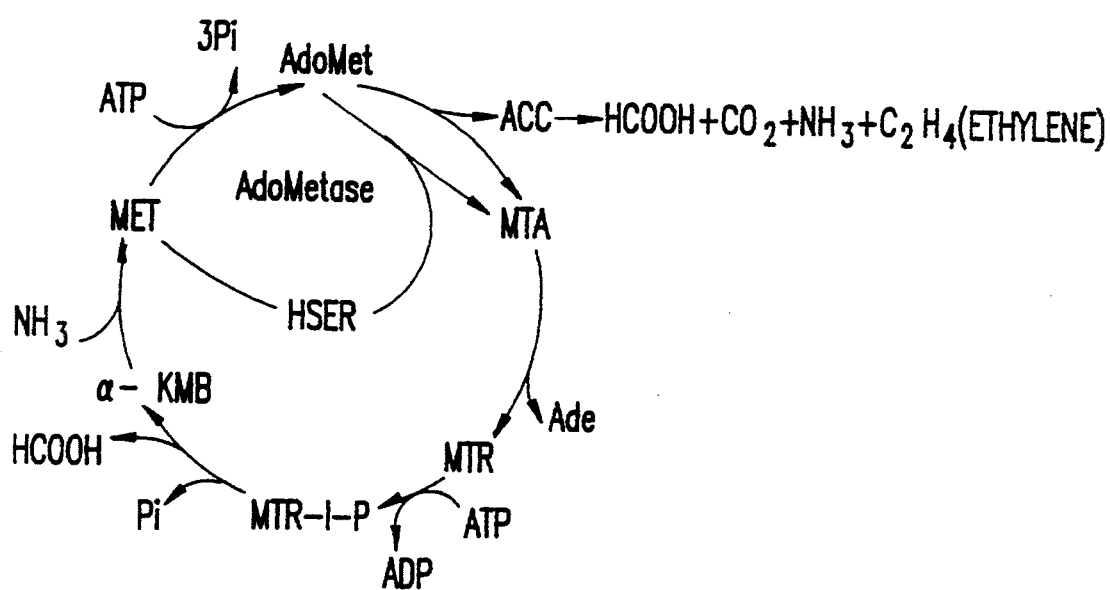
FIG. 1b schematically represents the ethylene biosynthetic pathway with AdoMetase.
Figure 1C:
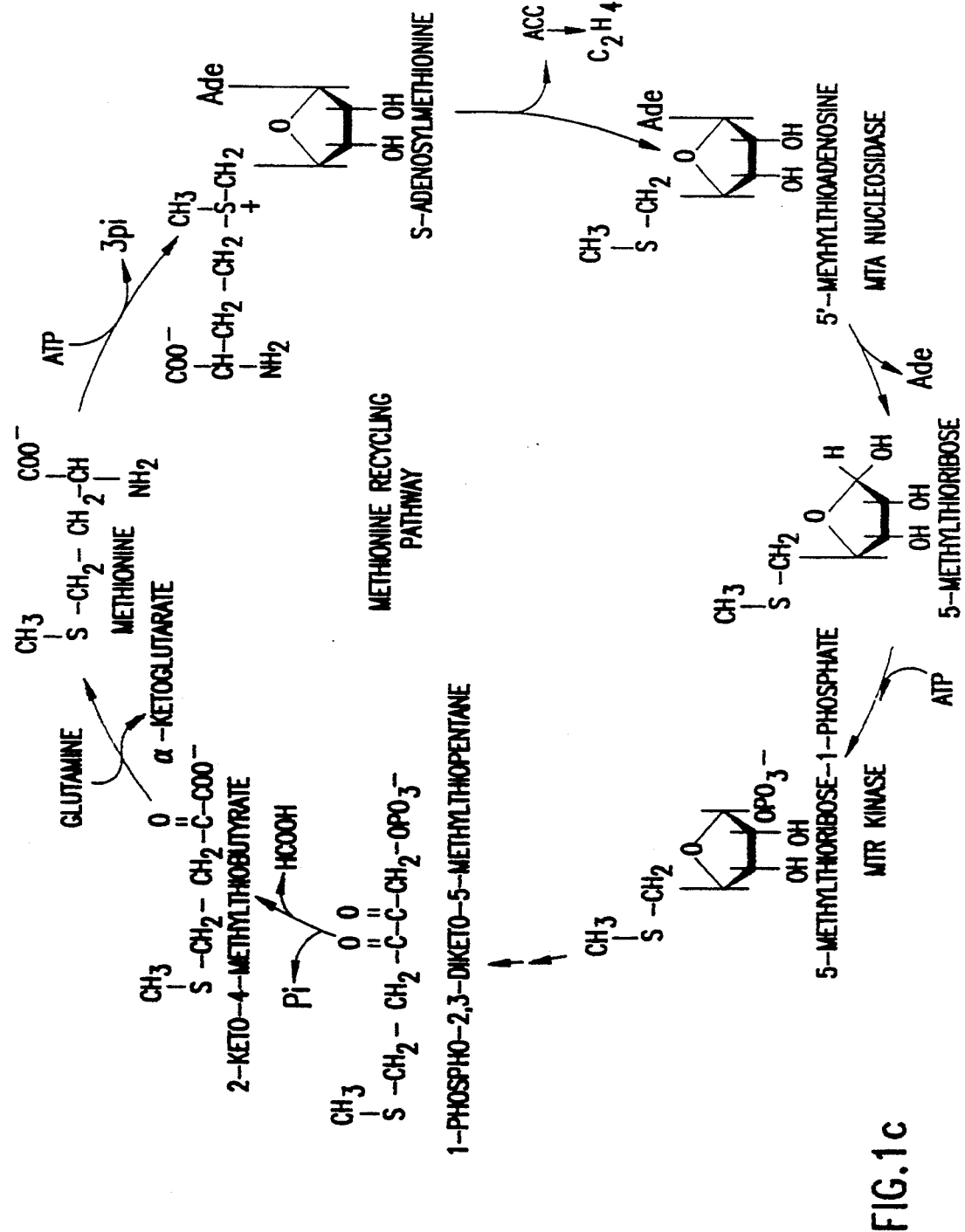
FIG. 1c schematically represents the methionine recycling pathway.

As seen in FIG. 1, the formation of ACC is a rate limiting step for production of ethylene in plant tissues. S. F. Yang, et al., "Ethylene Biosynthesis and Its Regulation in Higher Plants," *Ann. Rev. Plant Physiol,* 35:155–189, 1984. Various other methods may be employed to elicit transformation of the plant host, such as electroporation, microinjection, and microprojectile bombardment. These methods are well known in the art and detailed in the following representative references. T. M. Klein, et al., "Stable Genetic Transformation of Intact Nicotiana Cells by the Particle Bombardment Process," *Proc. Natl. Acad. Sci. USA*, Washington, D.C.: The Academy, Nov. 1988, vol. 85, Issue 22, pages 8502–8505, ill.; B. L. A. Miki, et al., "Microinjection: An Experimental Tool for Studying and Modifying Plant Cells," *Plant DNA Infectious Agents,* edited by Th. Hohn and J. Schell, Wien: Springer-Verlag, c1987, pages 249–265, ill.; C. Bellini, et al., "Transgenic Plants of Lettuce (Lactuca Sativa) Obtained Through Electroporation of Protoplasts," *Bio/Technol,* New York, N.Y.: Nature Publishing Co., May 1989, Vol. 7, Issue 5, pages 503–508, ill. An analogous PC2760/pBI121-AdoMetase clone containing the virG gene constituting a tripartite vector system is also employed to transform leaf discs by the method described above.

The present method is applicable to all higher plants, and particularly relevant for use with economically significant food crops and ornamentals. The following list of plant species to which the present method may be applied is representative of the wide range of applications, but is by no means limiting thereto.

Food crops:
Allium cepa (onion)
Allium sativum (garlic)
Ananas comosus (pineapple)
Ananas sativus (pineapple)
Apium graveolens (celery)
Asparagus officinalis (asparagus)
Beta vulgaris (red and sugar beets)
Brassica oleracea (cole crops)
Capsicum annum (peppers)
Capsicum frutescens (peppers)
Carica candamarcensis (papaya)
Carica cauliflora (papaya)
Carica papaya (papaya)
Cichorium endivia (endive)
Citrullus lanatus (watermelon)
Citrullus sp. (melons)
Citrulius vulgaris (watermelon)
Cucumis melo (cantaloupe)
Cucumis sativus (cucumber)
Cynara scolymus (Globe artichoke)
Daucus carota (carrots)
Ficus cadca (figs)
Fragaria sp. (strawberry)
Ragaria x ananassa (strawberry)
Lactuca sativa (lettuce)
Lycopersicon esculentum (tomato)
Malus pumila (apple)
Malus sylvestris (apple)
Musa acuminata (banana)
Musa cavendishii (banana)
Musa sp. (banana)
Olea europaea (olive)
Passiflora edulis (passion fruit)
Persea americana (avocado)
Phaseolus vulgaris (bean)
Phoenix dactylifera (date palm)
Pisum sativum (pea)
Prunus avium (cherry)
Prunus domestica (plum)
Prunus institia (plum)
Prunus mariana (prunus rootstock)
Prunus pandora (cherry)
Prunus persica (peach)
Prunus sp. (apricot, nectarines)
Punica granatum (pomegranate)
Pyris communis (pear)
Rubus idaeus (raspberry)
Rubus sp. (cane berries)
Rubus ursinus (raspberry)
Solanum melongena (eggplant)
Solanum tuberosum (potato)
Spinacla oleracea (spinach)
Vaccinium elliottii (blueberry)
Vaccinium macrocarpon (cranberry)
Vaccinium sp. (blueberry)
Vitis labruscana (concord grape)
Vitis rupestris (grape)
Vitis sp. (grapes)
Vitis vinifera (wine grapes)
Zea mays (corn)

Ornamentals:
Antirrhinum majus (snapdragon)
Chrysanthemum morifolium
Delphinium cardinale
Delphinium elatum Delphinium nudicaule
Dianthus caryophyllus (carnation)
Euphorbia pulcherrima (poinsettia)
Fuchsia hybrida
Gerbera jamesonii (daisy)
Gladiolus grandiflorus
Gladiolus hortulans
Homerocallis sp. (day lilly)
Iris hollandica
Iris sp.
Lilium sp. (lily)
Narcissus sp. (daffodil/narcissus)
Pelargonium hortorum (geranium)
Pelargonium peltatum (geranium)
Pelargonium sp.
Pelargonium zonale (geranium)
Petunia axillaris
Petunia hybrida
Petunia inflata
Petunia parodii
Petunia parviflore
Petunia sp.
Petunia tricuspidata
Rhododendron simsii (azalea)
Rhododendron sp.
Rosa canina
Rosa chinensis
Rosa damascena
Rosa hybrida
Rosa manetti
Rosa nitida
Rosa multiflora
Rosa sp.
Saintpaulia ionantha (african violet)
Tullpa gesneriana (tulip)
Orchids:
  Arachnis sp.
  Cattleya sp.
  Cymbidium sp.
  Dendrobium sp.
  Oncidium sp.
  Paphiopedilum sp.
  Vanda sp.

Figure 3:
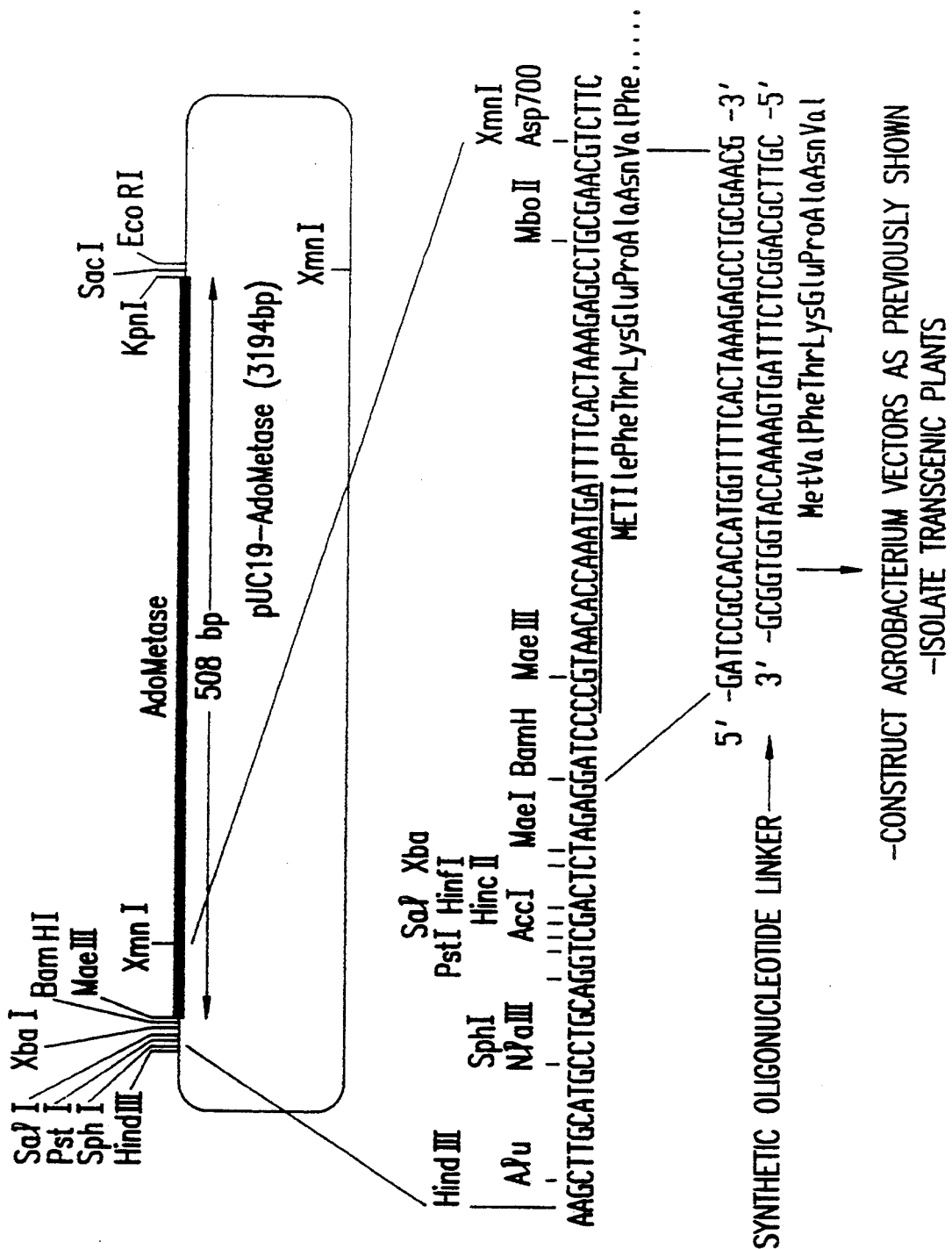
FIG. 3 schematically represents the genetic engineering of the AdoMetase gene.

The AdoMetase gene is genetically engineered further to achieve a preferred sequence. Analysis of the AdoMetase gene sequence indicated a less than optimal DNA sequence surrounding the initiation codon of the gene. According to the studies of M. Kozak, "At least Six Nucleotides Preceding the AUG Initiator Codon Enhance Translation in Mammalian Cells," *J. Mol. Biol.*, 196:947–950, 1987, a consensus initiation sequence for eucaryotic mRNAs exists which allows for efficient translation. The AdoMetase gene is genetically engineered to change the AdoMetase initiation sequence to the consensus Kozak sequence. The changes made to the DNA sequence are shown in FIG. 3 and carried out as follows.

EXAMPLE 3

The plasmid pUC19-AdoMetase is digested with Xmn I and Bam HI and the 1.9 kb and 1.3 kb fragments purified by electrolution after agarose gel electrophoresis. A double stranded synthetic oligonucleotide linker having the sequence indicated in FIG. 3 is ligated to the 1.9 kb fragment and this ligated DNA subjected to Xmn I digestion to remove excess linkers. The linkered 1.9 kb fragment is then repurified by electrophoresis on low melting temperature agarose and ligated to the 1.3 kb fragment to form the plasmid pUC19 SAM-K. The altered gene region is subjected to DNA sequence analysis and shown to contain the expected DNA sequence as shown in FIG. 6. This gene is named SAM-K and used to construct additional plant expression vectors. A pBI121-SAM-K (PC2760/pBI121-SAM-K) construction is created and transferred into tobacco using the approach described above in EXAMPLE 1. The plasmid DNA can also be used to directly transform the plant host via electroporation, microinjection, or microprojectile bombardment.

EXAMPLE 4

Figure 4:
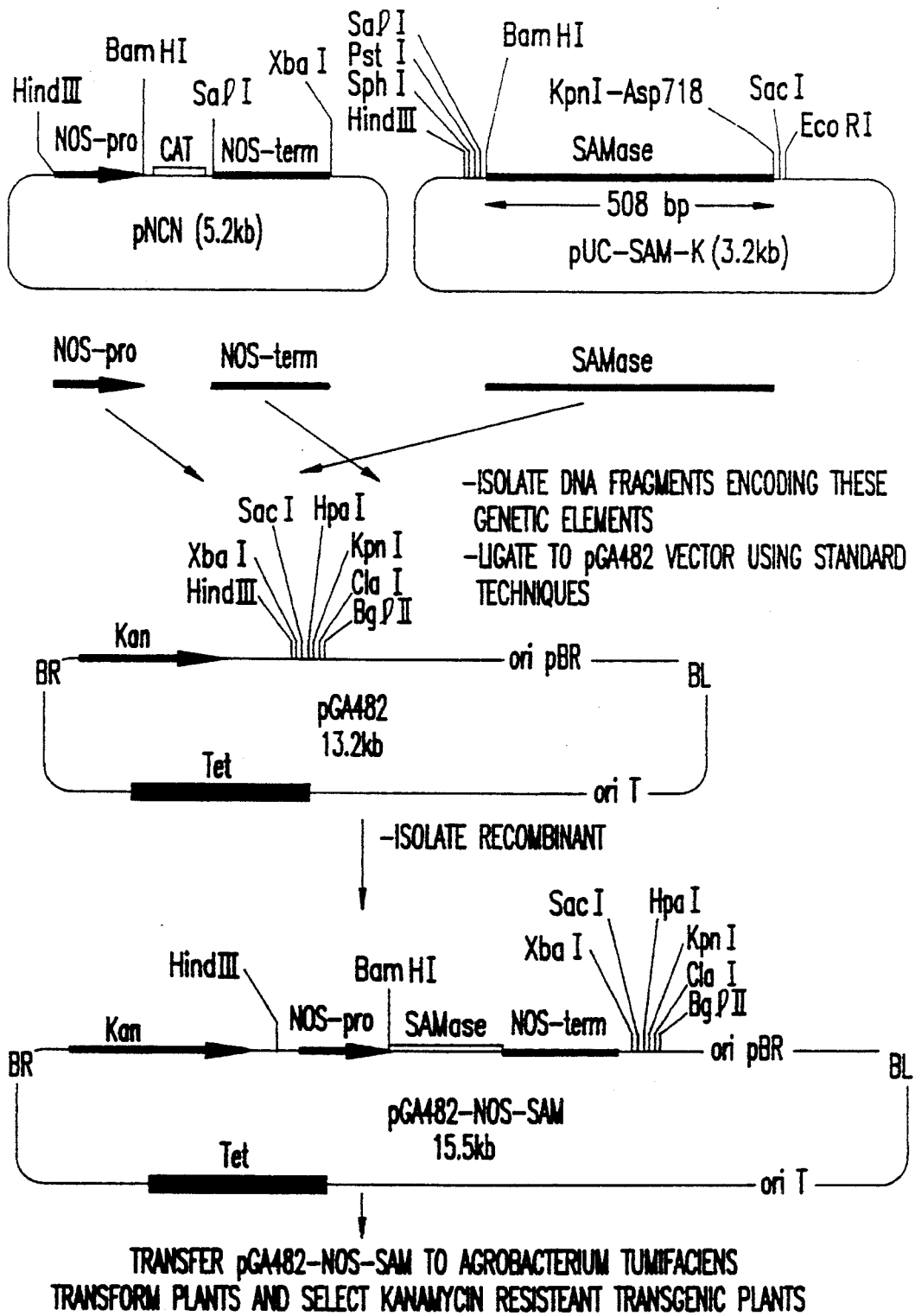
FIG. 4 schematically represents the alternative construction of pGA482-NOS-SAM.

The following Example discloses an alternative construction. FIG. 4 describes the construction of vector pGA482-NOS-SAM which is analogous to pBI121-AdoMetase or pBI121-SAM-K above. In this construction, a different promoter is employed as well as different parental plasmids. The parental plasmids are pGA482 and pNCN obtained from Pharmacia. The promoter used is the constitutive nopaline synthetase promoter (NOS-pro and NOS-term).

Using standard techniques, the DNA fragments NOS-pro and NOS-term are isolated from pNCN, and the SAMase fragment coding for the altered enzyme is isolated from pUC-SAM-K. The fragments are ligated into pGA482 at the appropriate restriction sites as indicated in the figure with the NOS-pro and NOS-term sequences flanking the SAMase fragment. The plasmid GA482-NOS-SAM is transferred to A. tumefaciens (PC2760/GA482-NOS-SAM) and used to transform plants as above.

While there is shown and described present preferred embodiments of the invention, it is to be distinctly understood that the invention is not limited thereto, but may be otherwise variously embodied and practiced within the scope of the following claims.

We claim:

1. A method for reducing ethylene biosynthesis in plant cells, comprising:
   providing a vector encoding (i) a first DNA sequence encoding a gene encoding a selectable marker functional in plant cells, where said first DNA sequence is flanked by regulatory elements effective to allow expression of the sequence in a plant host, and (ii) a second DNA sequence which is flanked by regulatory elements effective to allow expression of the sequence in a plant host, and where said second DNA sequence encodes a S-adenosylmethionine hydrolase enzyme which (a) hydrolyzes S-adenosylmethionine to homoserine and 5'-methylthioadenosine, and (b) is derived from *E. coli* bacteriophage T3, and
   transforming plant host cells with said vector, wherein the transformed plant host cells are capable of expressing said enzyme.

2. The method of claim 1, where said second DNA sequence encodes the protein sequence presented in FIG. 6.

3. The method of claim 1, wherein the transformation of a plant host is carried out by a direct transformation methodology selected from the group consisting of electroporation, microinjection, and microprojectile bombardment.

4. The method of claim 1, wherein said gene encoding a selectable marker functional in plant cells confers kanamycin resistance.

5. The method of claim 1, wherein said regulatory elements flanking the second DNA sequence include a plant promoter and where said plant promoter is a constitutive nopaline synthetase promoter.

6. The method of claim 1, wherein said regulatory elements flanking the second DNA sequence include a plant promoter and where said plant promoter is a constitutive expression promoter.

7. The method of claim 6, wherein said constitutive expression promoter is a Cauliflower Mosaic Virus promoter.

8. The method of claim 1, wherein said plant host is Nicotiania tabacum L. cv. Wisconsin.

9. A transgenic plant encoding
a DNA sequence which encodes and expresses a S-adenosylmethionine hydrolase enzyme, where said enzyme (i) can hydrolyze S-adenosylmethionine to homoserine and 5'-methylthioadenosine, and (ii) is derived from *E. coli* bacteriophage T3.

10. A vector useful for transformation of a plant host, said vector comprising
a first DNA sequence encoding a gene encoding a selectable marker functional in plant cells, where said first DNA sequence is flanked by regulatory elements effective to allow expression of the sequence in a plant host, and where said vector further comprises
a second DNA sequence which (i) is flanked by regulatory elements effective to allow expression of the sequence in a plant host, and (ii) encodes a S-adenosylmethionine hydrolase enzyme which (a) hydrolyzes S-adenosylmethionine to homoserine and 5'-methylthioadenosine, and (b) is derived from *E. coli* bacteriophage T3.

* * * * *